(12) United States Patent
Pascal (10) Patent No.: US 9,360,605 B2
(45) Date of Patent: Jun. 7, 2016

(54) SYSTEM AND METHOD FOR SPATIAL AND SPECTRAL IMAGING (71) Applicant: GIVEN IMAGING LTD., Yogneam (IL)

(72) Inventor: Amit Pascal, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 333 days.

(21) Appl. No.: 13/743,469

(22) Filed: Jan. 17, 2013

(65) Prior Publication Data

US 2013/0190563 A1     Jul. 25, 2013

Related U.S. Application Data

(60) Provisional application No. 61/588,787, filed on Jan. 20, 2012.

(51) Int. Cl.
| | |
|---|---|
| *A61B 1/04* | (2006.01) |
| *A61B 1/06* | (2006.01) |
| *G02B 5/20* | (2006.01) |
| *H04N 5/232* | (2006.01) |

(Continued)

(52) U.S. Cl.
CPC ............ *G02B 5/201* (2013.01); *A61B 1/00186* (2013.01); *A61B 1/00188* (2013.01); *A61B 1/041* (2013.01); *H04N 5/23212* (2013.01); *G02B 27/0075* (2013.01); *G02B 2207/129* (2013.01)

(58) Field of Classification Search
CPC ...... A61B 1/041; A61B 1/043; A61B 1/0638; A61B 1/0646; A61B 1/00186; A61B 5/0059
USPC ......... 600/109, 160, 130, 167, 168, 176, 181; 348/65, 68, 70
See application file for complete search history.

(56) References Cited

U.S. PATENT DOCUMENTS

| | | | | |
|---|---|---|---|---|
| 6,069,651 | A | * | 5/2000 | Tsuyuki ............. G02B 23/2484 348/65 |
| 2003/0158503 | A1 | * | 8/2003 | Matsumoto ................... 600/593 |

(Continued)

OTHER PUBLICATIONS

Wagadarikar et al; Video rate spectral imaging using a coded aperture snapshot spectral imager; dbrady@duke.edu; http://www.disp.duke.edu, 2009 Optical Society of America.

(Continued)

*Primary Examiner* — Thomas J Sweet
*Assistant Examiner* — William Chou
(74) *Attorney, Agent, or Firm* — Pearl Cohen Zedek Latzer Baratz LLP (57) ABSTRACT

A system and method for acquiring images containing spatial and spectral information of an object include acquiring defocused images using an optical system based on extended depth of field. The optical system further includes a filter array comprising an array of at least six different sub-filters that are arranged such that any group of four immediately adjacent sub-filters includes at least one red sub-filter, at least one green sub-filter and at least one blue sub-filter. The filter array is located at the aperture stop of the optical system. A coded mask is located at the focal plane of the optical system, and an imager is located beyond the focal plane such that images acquired by the imager are defocused. The images are refocused, and spectral and spatial information is restored by designated software.

16 Claims, 8 Drawing Sheets

(51) Int. Cl.
*A61B 1/00* (2006.01)
*G02B 27/00* (2006.01)

(56) References Cited

U.S. PATENT DOCUMENTS

2004/0079890 A1* 4/2004 Fraser et al. ............. 250/370.11
2006/0184040 A1* 8/2006 Keller et al. ................. 600/476

OTHER PUBLICATIONS

Horstmeyer et al: Flexible Multimodal Camera Using a Light Field Architecture; Stanford University; The MITRE Corporation; Nov. 12, 2008.
Horstmeyer et al; Modified light field architecture for reconfigurable multimode imaging, The MITRE Corporation, 7515 Colshire Dr., Mclean, VA 22102; SPIE Digital Library; vol. 7468; Nov. 18, 2009.

* cited by examiner

SYSTEM AND METHOD FOR SPATIAL AND SPECTRAL IMAGING

CROSS REFERENCE TO RELATED APPLICATIONS

This Application claims the benefit of U.S. Provisional Application Ser. No. 61/588,787, filed Jan. 20, 2012, which is hereby incorporated by reference in its entirety.

FIELD OF THE INVENTION

The present invention relates to the field of imaging. In particular, the present invention relates to a system and method for acquiring images of an object, while providing multi-band spectral information as well as spatial information of the object.

BACKGROUND OF THE INVENTION

Imaging an object may be considered as a collection of points from the plane of the object that are being focused by an optical system onto a collection of points on the plane of an image sensor. When there is a need to obtain spectral information as well as spatial information of the object, there is a fundamental problem, since this task is essentially the need to simultaneously capture a two-dimensional image of the object plane together with the color of each point of the object plane, this being essentially a "third dimension" of the object plane, and to record these three dimensions of information on the two-dimensional plane of the image sensor. A number of proposed solutions have been suggested in the prior art to solve this problem.

One of the possible optical systems may be one that includes an array of pinholes that may be positioned at the focal plane of the light reflected off the object, while the image sensor is located beyond the focal point such that the image acquired is defocused (and would be later focused by appropriate software). The pinhole array is used to differentiate between points from the plane of the object, such that there won't be any overlap of points in the plane of the image sensor. Without the pinholes there is overlap between points on the imager's plane, which would make it practically impossible to correlate between points on the imager's plane to points on the object's plane and thus practically impossible to restore the spatial information of the object.

A filter array comprising sub-filters may be added to the system and may be positioned at the aperture stop, such that spectral information may be acquired by the optical system as well as spatial information. That is, every pixel at the imager's plane has two "coordinates"; one for the angle at which light was reflected off the object, and a second for the sub-filter which the light reflected off the object passed through. However, the main disadvantages of using a pinhole array is losing spatial information, and losing light when collecting the light reflected off the object, since the pinhole array blocks some of the light reflected off the object from being projected onto the imager. One of the groups implementing such an optical system is, for example, the MITRE Corporation, Mclean, Va. (Horstmeyer R., Athale R. and Euliss G. (2009) "Modified light field architecture for reconfigurable multimode imaging". Proc. of SPIE, Vol. 7468, 746804).

Another possible optical system that may be used to create an image of an object while providing spatial and spectral information is one where instead of a filter array located at the aperture stop, a mask is located at the aperture stop. The mask, according to Wagadarikar et al. a group from Duke University, Durham, N.C., USA, is called a 'coded aperture' (A. A. Wagadarikar, N. P. Pitsianis, X. B. Sun and D. J. Brady (2009). "Video rate spectral imaging using a coded aperture snapshot spectral imager." Optics Express 17(8): 6368-6388). The optical system described in this article does not comprise a pinhole array so there is an overlap between pixels of the image sensor. The mask is random with the requirement of being 50% open for passage of light that is reflected off the imaged object. With this optical system there is minimal loss of spatial resolution, since the scenes that are being imaged do not consist of dramatic spectral changes, and the objects are relatively large so it is not difficult to distinguish between areas of the same spectra.

The mask, according to the above optical system, provides combinations of spatial and spectral "coordinates" that may describe the object. (The "coordinates" are acquired by the imager followed by software reconstruction, in order to focus the acquired images). In areas of the object where the spectrum is substantially similar, only the spatial data is missing. The mask is then used to separate between close points with similar spectrum on the imager's plane, so it would be easier to correlate those points to points on the object's plane. However, when close points on the object have different spectrum (e.g., along the edges of the object) it is more difficult to distinguish between the points projected onto the imager.

Images that provide spatial as well as spectral information may be important within small scale in-vivo imaging devices, e.g., endoscopes and capsule endoscopes. Spatial information is needed in order to determine the in-vivo location of the device, and spectral information of in-vivo tissue is important for determining various diseases at early stages that may be expressed in changes in spectra of various in-vivo particles, e.g., hemoglobin. There is therefore a need for a new optical system that may be implemented into devices that are to be inserted in-vivo, in order to acquire images that contain both spatial and spectral information.

SUMMARY OF THE INVENTION

In order to implement an optical system providing spatial and spectral information into in-vivo devices, a few changes should be made to the optical systems described above.

According to some embodiments of the present invention, the optical system is based on Extended Depth Of Field (EDOF) optical systems, in order to substantially remove the dependency of the size of the spot of light reflected off the object and projected onto the imager, and changes in spectral mapping, on the distance between the object and the optical system. Furthermore, in some embodiments of the present invention, the optical system may comprise a filter array with a special arrangement of the sub-filters of the array. The arrangement of the sub-filters may be such that any group of four immediately adjacent sub-filters includes at least one red sub-filter, at least one green sub-filter and at least one blue sub-filter. The filter array is typically located at the aperture stop of the optical system of the invention.

According to some embodiments, A system for acquiring images containing spatial and spectral information of an object may comprise an extended depth of field optical system, a filter array comprising an array of at least six different sub-filters that may be arranged such that any group of four immediately adjacent sub-filters comprises at least one red sub-filter, at least one green sub-filter and at least one blue sub-filter. The filter array may be located at the aperture stop of the optical system. The optical system may further comprise a coded mask that is located at the focal plane of the optical system, and an imager that may be located beyond the focal plane such that images acquired by the imager are defocused.

In some embodiments, the filter array comprises nine different sub-filters. In other embodiments, the filter array may comprise six different sub-filters, and three different sub-filters that each is a duplicate of one of the six different sub-filters.

In some embodiments, the sub-filters of the filter array may be selected from wavelengths that correspond to absorption spectra of hemoglobin. The sub-filters may be selected from the following wavelengths: 420, 470, 510, 540, 560, 570, 600, 620, 630, 660, 800, and 880 nm.

In some embodiments, the coded mask may be a random mask. According to some embodiments, the coded mask may be between 40% to 60% transmissive and, respectively, between 60% to 40% closed for passage of light. For example, in some embodiments, the coded mask may be 50% transmissive for passage of light. Other random masks may be used. In some embodiments, the coded mask may comprise hyper-pixels arranged at groups of three over three hyper-pixels. The coded mask may be arranged such that for any three over three hyper-pixels at least one hyper-pixel is open and at least one hyper-pixel is closed.

According to some embodiments, the focal plane of the system may be located at the top end of the cover glass of the imager. The imager may be a black and white imager.

In some embodiments, a capsule endoscope may comprise the optical system described above, while the location of the focal plane may be at the top end of the cover glass or inside the cover glass, and the coded mask may be located at the top end of the cover glass.

According to some embodiments, a method for acquiring images containing spatial and spectral information of an object may comprise the steps of: acquiring defocused images using the system described above, refocusing the acquired images, and restoring spatial and spectral information of the object according to the location of the imager's pixel that collected the light, and according to the wavelength of the light collected by the imager, respectively. In some embodiments, the step of refocusing of the images may be performed by designated software. In some embodiments, the step of restoring spatial and spectral information of the object may be performed by designated software, either the same software that performs refocusing of the images or different software.

BRIEF DESCRIPTION OF THE DRAWINGS

The present invention will be understood and appreciated more fully from the following detailed description taken in conjunction with the appended drawings in which.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

The system and method described with respect to embodiments of the present invention provide acquisition of images containing both spatial and spectral information of the imaged object.

Figure 1:
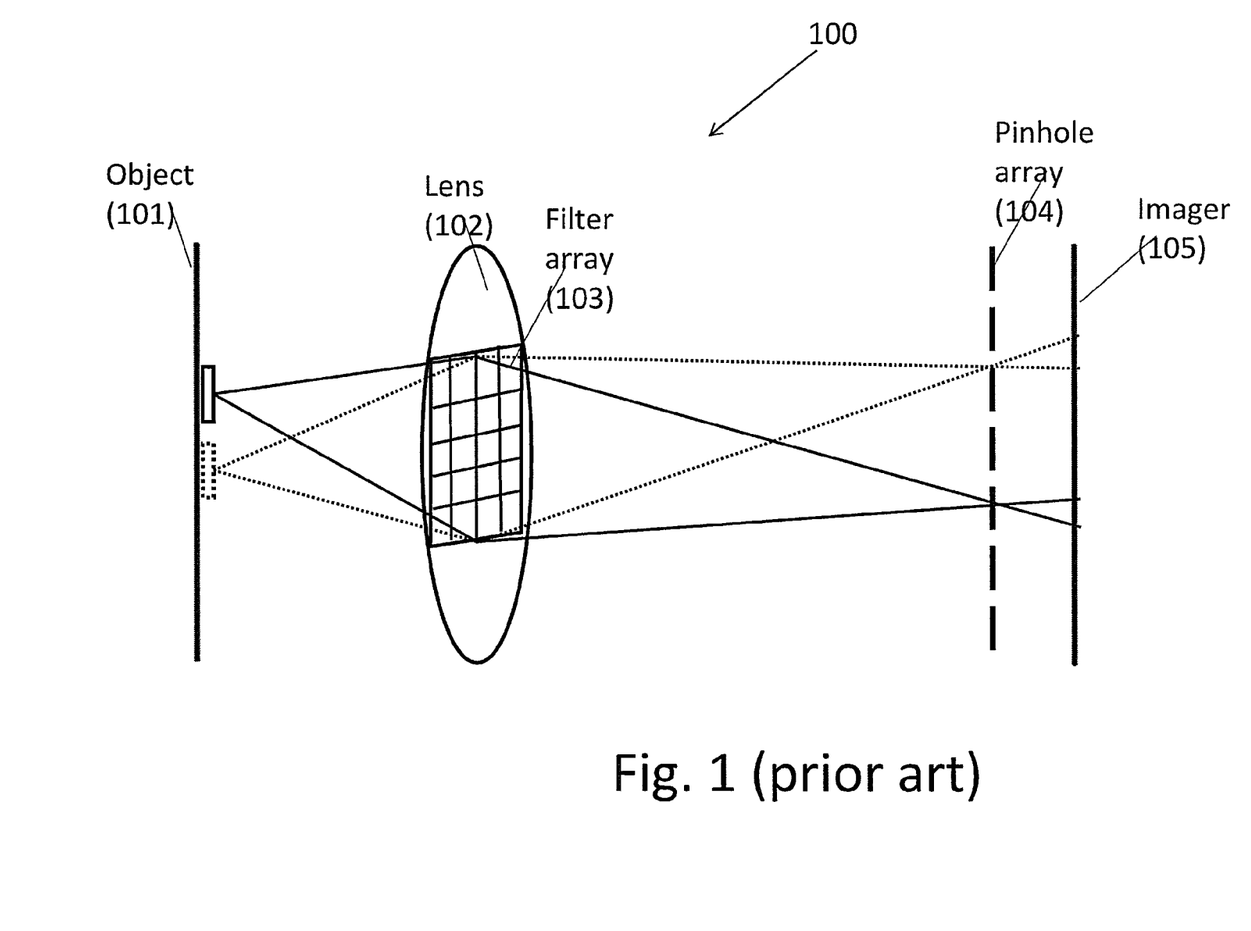
FIG. 1 is a schematic illustration of a first optical system, in accordance with the prior art.

Reference is now made to FIG. 1, which schematically illustrates a first optical system according to the prior art. Optical system 100 of the prior art comprises lens 102 and filter array 103, both of which are located at the aperture stop of the optical system 100. Optical system 100 further comprises a pinhole array 104, which is located at the focal plane of optical system 100, and imager 105, which is located beyond the focal plane of system 100, such that images acquired by imager 105 are defocused. The defocused images may later be refocused using appropriate software.

The pinhole array 104 is used to differentiate between points from the plane of the object 101, such that there isn't any overlap of points in the plane of the imager 105. Without the pinhole array 104 there would be overlap between points on the plane of imager 105, which would make it practically impossible to correlate between points on the plane of imager 105 to points on the plane of the object 101 and thus practically impossible to create a substantially accurate image of the object.

Filter array 103 is composed from a plurality of sub-filters. Filter array 103 is positioned at the aperture stop of optical system 100, such that spectral information may be acquired by optical system 100, as well as spatial information. That is, every pixel at the plane of imager 105 has two "coordinates"; one for the angle at which light was reflected off object 101, and a second for the sub-filter which the light reflected off object 101 passed through. However, the main disadvantages of using a pinhole array, e.g., pinhole array 104, is losing spatial information, and losing light when collecting the light reflected off the object, e.g., object 101, since the pinhole array blocks some of the light reflected off the object from being projected onto the imager, e.g., imager 105. Only part of the light reflected off the object passes through pinhole array 104, since only light that reaches the pinholes of pinhole array 104 may in fact pass through pinhole array 104.

Figure 2:
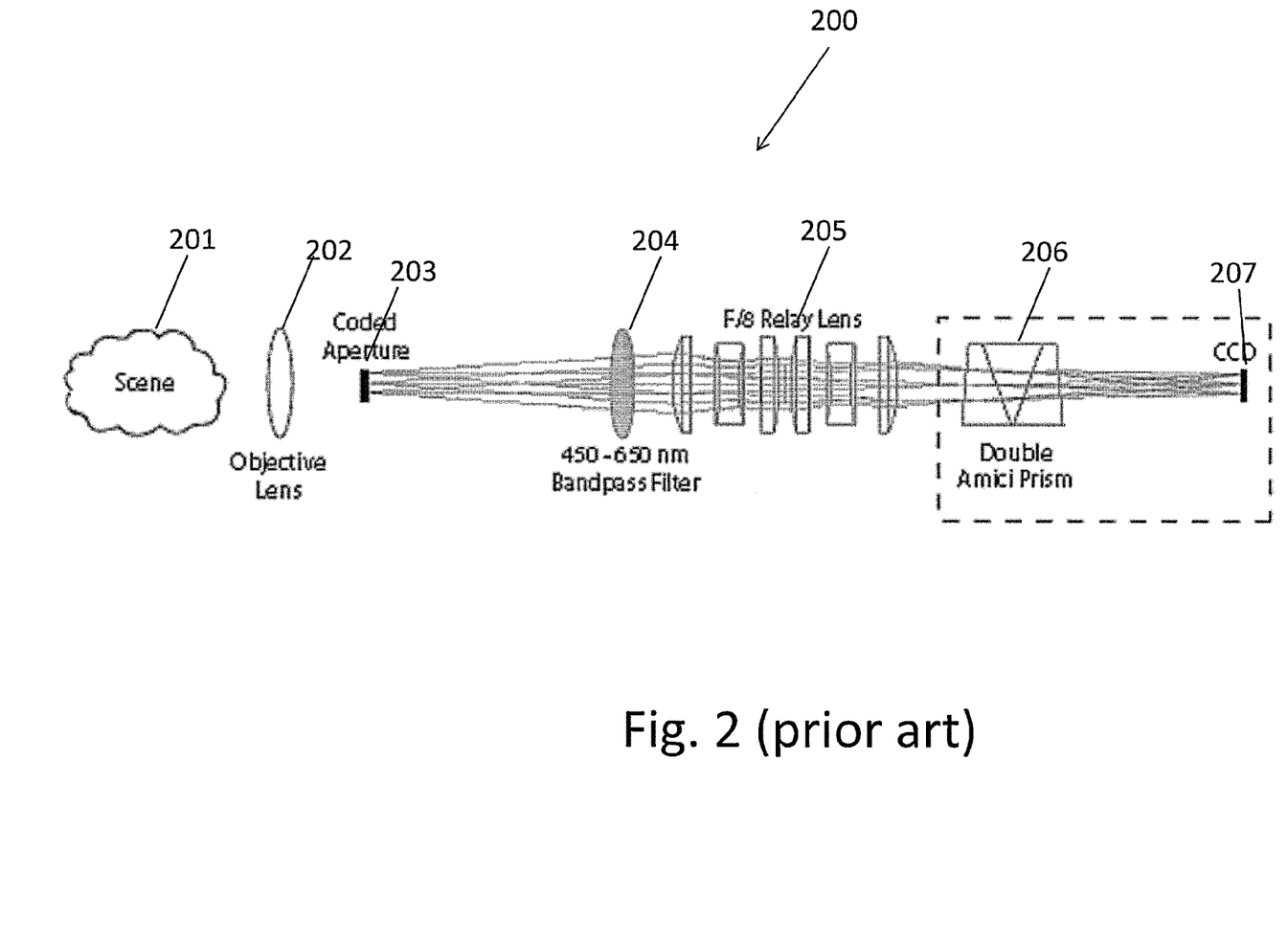
FIG. 2 is a schematic illustration of a second optical system, in accordance with the prior art.

Reference is now made to FIG. 2, which schematically illustrates a second optical system, in accordance with the prior art. Optical system 200 comprises objective lens 202, coded aperture or coded mask 203 that is located at the aperture stop, band-pass filter 204 (for limiting the range of wavelengths that would reach the imager 207), relay lenses 205, prism 206 (for providing a wide and continuous range of spectra) and imager 207. Optical system 200 does not comprise a pinhole array as does optical system 100, so typically there should be overlap between points on the plane of the imager 207, which would make it difficult to restore their location on the plane of the object, e.g., object 201. However, optical system 200 comprises a mask 203. Mask 203 is a random mask, which is 50% open for transfer of light, that is, only 50% of the light that reaches mask 203, passes through it.

Every pixel at the plane of imager 207 has two "coordinates"; one for the angle at which light was reflected off the object 201, and a second for the wavelength of the light reflected off object 201, which passed through prism 206. Optical system 200 is mainly useful when used to image scenes that do not involve major changes in spectra throughout the scene. Therefore, mask 203 is used to differentiate between adjacent points on the plane of object 201, which have similar spectra, and which due to the mask, appear as different points on the plane of imager 207. However, when adjacent points on the plane of object 201 have different spectra, it is more difficult to correlate between points on the plane of imager 207 to points on the plane of object 201, since in this case both the spatial and the spectral information are missing.

Figure 3:
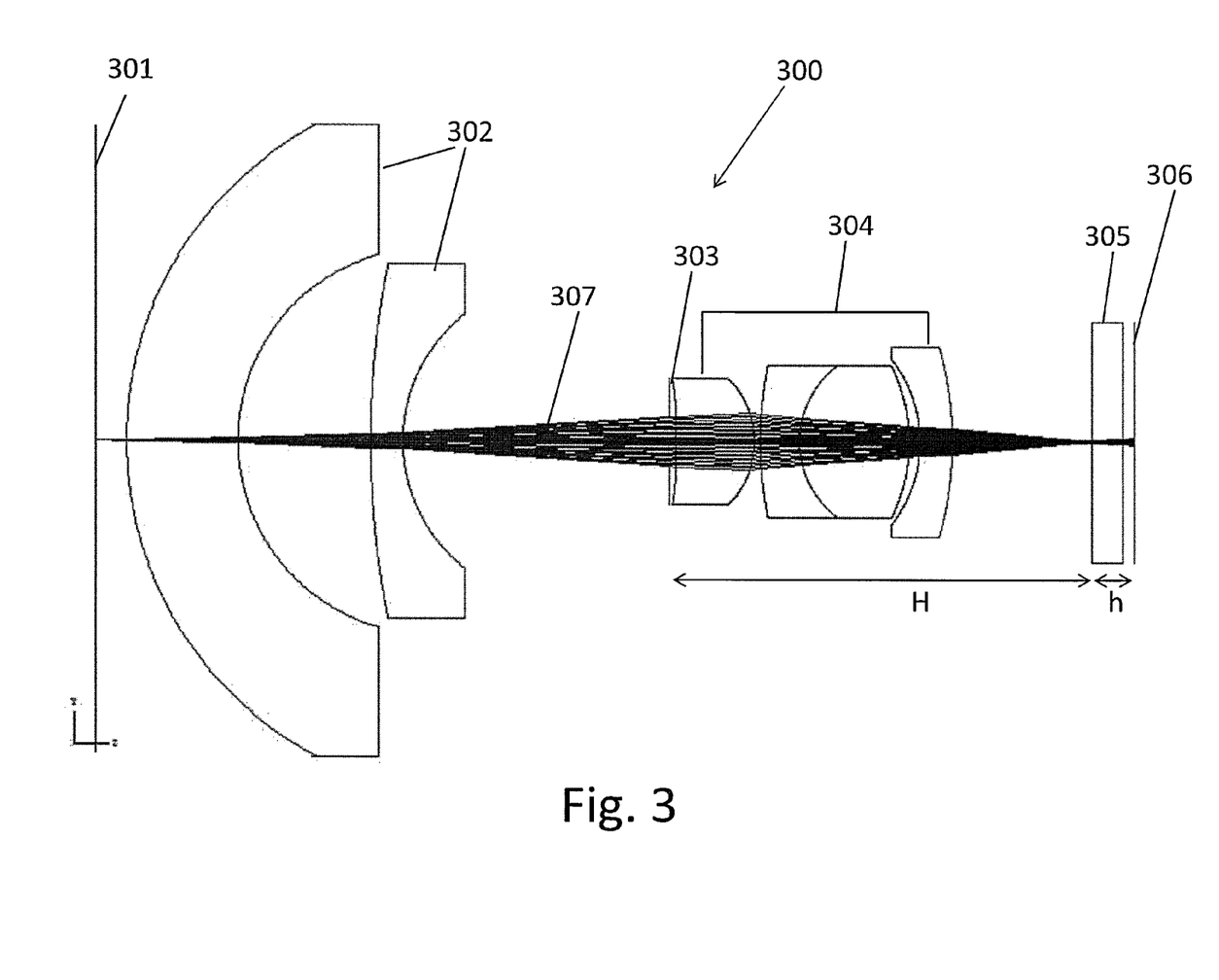
FIG. 3 is a schematic illustration of an optical system based on extended depth of field for acquiring images containing both spatial and spectral information of an object, in accordance with embodiments of the present invention.

Reference is now made to FIG. 3, which schematically illustrates an optical system according to embodiments of the present invention, which enables acquisition of images of an object, which contain both spatial and spectral information of the object. As will be described in details hereinbelow, the optical system according to embodiments of the present invention differs from the prior art in at least three major aspects. One difference is that the optical system may be based on Extended Depth Of Field (EDOF) optical system with the addition that the focal plane may be located at the top end of the cover glass of the imager, i.e., at the end of the cover glass that is farthest from the imager (or it may be located inside the cover glass) instead of on the imager, as in classic EDOF systems. Another difference is that instead of using a pinhole array, a mask may be used but at a different location than proposed by the prior art. According to embodiments of the present invention, the mask may be located at the focal plane instead of at the aperture stop. And additional major difference is in the arrangement of the filter array located at the aperture stop. According to embodiments of the present invention, the filter array may be arranged such that any combination of four immediately adjacent sub-filters comprises at least one sub-filter selected from the red spectra, which allows passage of light of the selected red spectrum, at least one sub-filter selected from the green spectra, which allows passage of light of the selected green spectrum, and at least one sub-filter selected from the blue spectra, which allows passage of light of the selected blue spectrum. In some embodiments, the sub-filters are selected from wavelengths that correspond to the absorption spectra of hemoglobin; therefore, the filter array may enable acquisition of an image of in-vivo tissue containing spectral information relevant to the pathological condition of the tissue.

As shown in FIG. 3, optical system 300 may comprise objective lens 302, and filter array 303 for providing spectral information. The filter array 303 may be located at the aperture stop of optical system 300. Filter array 303 may be composed of sub-filters, as will be described in details with regards to FIG. 5. Optical system 300 may further comprise a set of field lenses 304, and imager 306 with cover glass 305 placed in front of it, between imager 306 and field lenses 304. The path of light reflected off a certain point of object 301, and which passes through optical system 300 until it is projected onto imager 306 is depicted as light rays 307. Light rays 307 are only one example of many other light rays that may be reflected off other points of object 301.

Optical system 300 may be designed as Extended Depth Of Field (EDOF) optical system, with one change from classic EDOF systems. In classic EDOF optical systems the focal plane is on the imager, i.e., the images acquired by classic EDOF systems are focused. However, in optical system 300 the focal plane is not on the imager 306 but rather on the top end of cover glass 305, i.e., on the end/side of the cover glass that is farthest from imager 306. That is, images acquired by imager 306 are defocused.

Defocusing of the images acquired by imager 306 is necessary in order for the images to contain both spatial and spectral information of the object (e.g., object 301). If the images were to be focused at the plane of imager 306, any ray of light reflected off a certain point of object 301, would eventually be focused onto substantially the same imager's pixel. This would make it practically impossible to determine through which sub-filter (of filter array 303) the light ray passed, which means it would be practically impossible to acquire spectral information. By placing imager 306 beyond the focal plane such that images acquired by imager 306 are defocused, the information on the angle of the reflected light may be determined, thus spectral information may be determined.

Furthermore, standard cameras are designed to acquire images from infinity, whereas small scale devices, e.g., capsule endoscopes or traditional endoscopes, need to acquire images from close distances. In close distances, the location of the focal plane changes with correlation to the distance between the imaged object and the optical system (or between the object and the aperture stop, or between the object and the imaging device comprising the optical system). If the location of the focal plane of the optical system changes, the spectral mapping is different for the same object positioned at different distances from the optical system. For different distances of the (same) object from the optical system, the light would be projected or collected by different pixels of the imager, which would affect the spectral information collected by the imager and the size of the spot of light projected onto the imager. Therefore, an EDOF optical arrangement with defocusing at the plane of imager 306 may be used (e.g., in small scale devices) so as to ensure that objects at substantially any distance from imager 306 would be defocused at the same amount. As shown in FIG. 3, at the top end of cover glass 305, (which is the end of cover glass 305 farthest from imager 306), light rays 307 are not focused at one point but rather light rays 307 are focused along a distance prior to and at the top end of cover glass 305. That distance along which light may be focused at, may ensure that the size of the spot of light projected onto imager 306, as well as the spectral information stay the same for substantially any distance between object 301 and optical system 300. According to some embodiments, a coded mask may be located at the focal plane of optical system 300. According to FIG. 3, the focal plane is located at the top end of cover glass 305; therefore, a coded mask may be positioned at the top end of cover glass 305 of imager 306.

In some embodiments, the coded mask may be randomly selected. In other embodiments, the coded mask may have several requirements other than being completely random, e.g., that no pattern would be created by the mask. In some embodiments, the mask may be between 40% to 60% transmissive for light reflected off an object to pass through it, and thus, respectively, between 60% to 40% closed to prevent light reflected off the object to pass through it. For example, the coded mask may be 50% transmissive for passage of light. According to embodiments of the invention, the coded mask may comprise hyper-pixels arranged at groups of three-over-three hyper-pixels (which may correspond to a filter array comprising nine sub-filters, as will be described in details with regards to FIG. 5). Furthermore, the coded mask may be arranged such that for any combination of three-over-three hyper-pixels, at least one hyper-pixel is open and at least one hyper-pixel is closed.

The mask may be used to separate between points that are close to one another on the plane of the object. Assuming the imaged object has substantially uniform spectra, as common, for example, in the gastrointestinal (GI) tract, the main information that could be extracted from the image while using the mask, may be related to spatial information of the object. In the GI, for example, the main changes within an imaged scene are spatial changes, whereas the spectrum of the scene is substantially uniform. After light that is reflected off the object passes through the mask and onto the imager, the acquired image requires reconstruction in order to determine the "real" image of the object. The effect of the mask may be determined from images of scenes that are substantially uniform both spatial and spectral wise. According to the effect of the mask, several "solutions" of how the real image of the object is may be available. When implementing optical system 300 within small scale in-vivo devices, e.g., devices that may be inserted into the GI tract, various assumptions, e.g., assumptions related to GI scenes (such as that GI scenes are typically uniform spectral wise), may be used in order to dilute the number of possible solutions.

Furthermore, when implementing optical systems, as optical system 300, into small scale in-vivo devices, few adjustments should be made. For example, the distance H (shown in FIG. 3) is defined as the distance between the aperture stop (e.g., aperture stop where filter array 303 is located) and the focal plane (e.g., located at the end of cover glass 305, which is the end farthest from imager 306). Distance h is defined as the distance between the focal plane (e.g., located at the end of cover glass 305, which is the end farthest from imager 306) and the imager 306. These two distances h and H are relevant to the size of each of the pixels of the imager (e.g., imager 306) and to the size of each of the sub-filters of the filter array (e.g., filter array 303), as shown in the following equation:

$$\frac{sub_{filter} \cdot h}{H} \geq \text{pixel} \qquad (1)$$

In large scale devices, the ratio between h and H may be around 1:200, whereas, for example, h=1.5 mm, and H=300 mm. The same ratio should be maintained in small scale devices, in order to acquire images of a similar size as in large scale devices; however, the restriction of the size of small scale devices should also be taken under consideration. Therefore, if H, which may be restricted, for example, by the size of a lens assembly of a capsule endoscope, equals 2-3 mm, then h should be equal to 0.01-0.015 mm. The distance h between the focal plane and the imager is thereby very limited in size. One of the possible solutions for achieving such a small distance h may be by using a very thin coating on the imager's silicon chip, instead of using a cover glass. However, other solutions may be used.

Figure 4A:
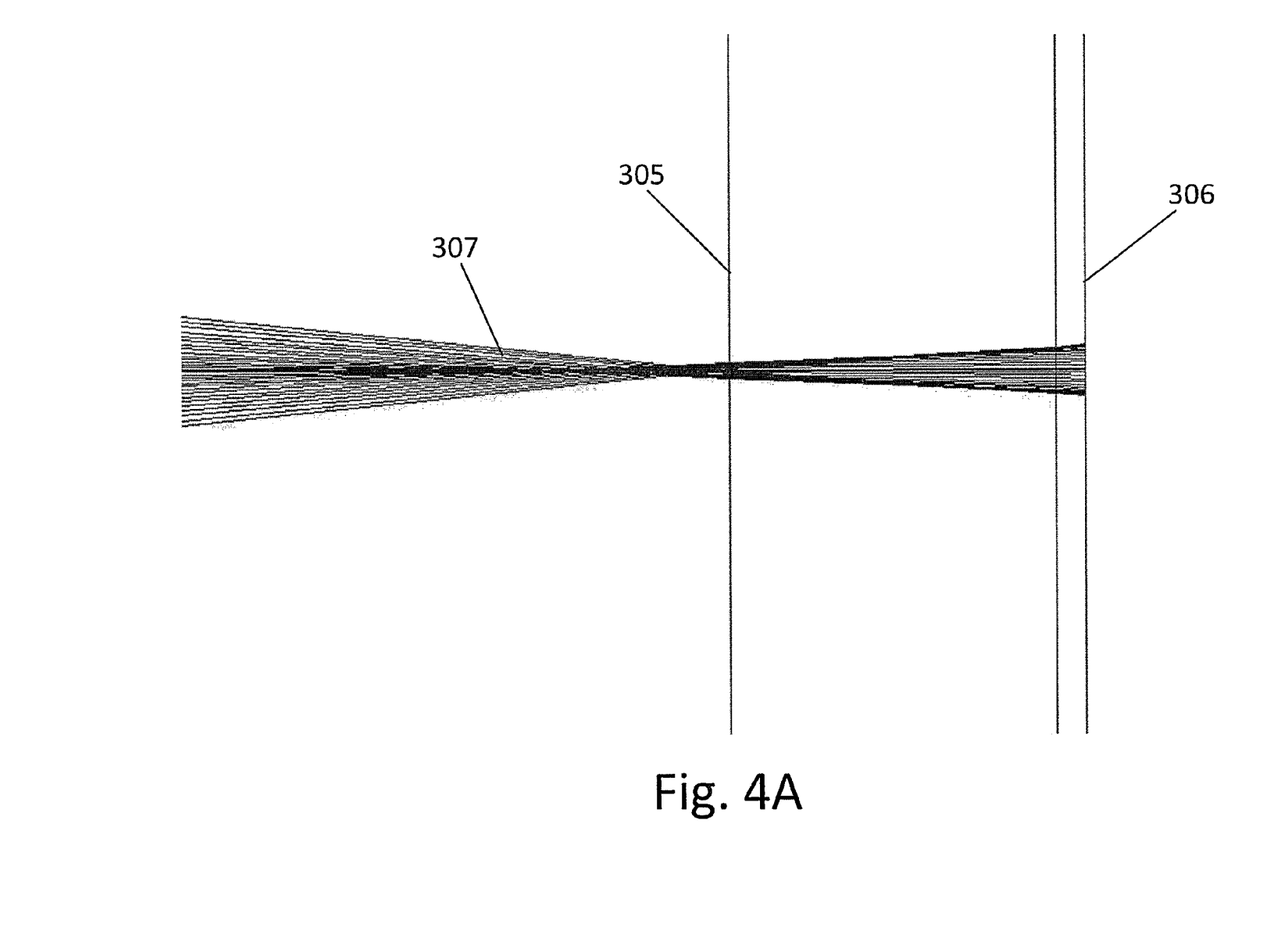
FIGS. 4A-4B are schematic illustrations of a focal plane located at the top end of the cover glass and a focal plane located inside the cover glass, respectively, in accordance with embodiments of the present invention.
Figure 4B:
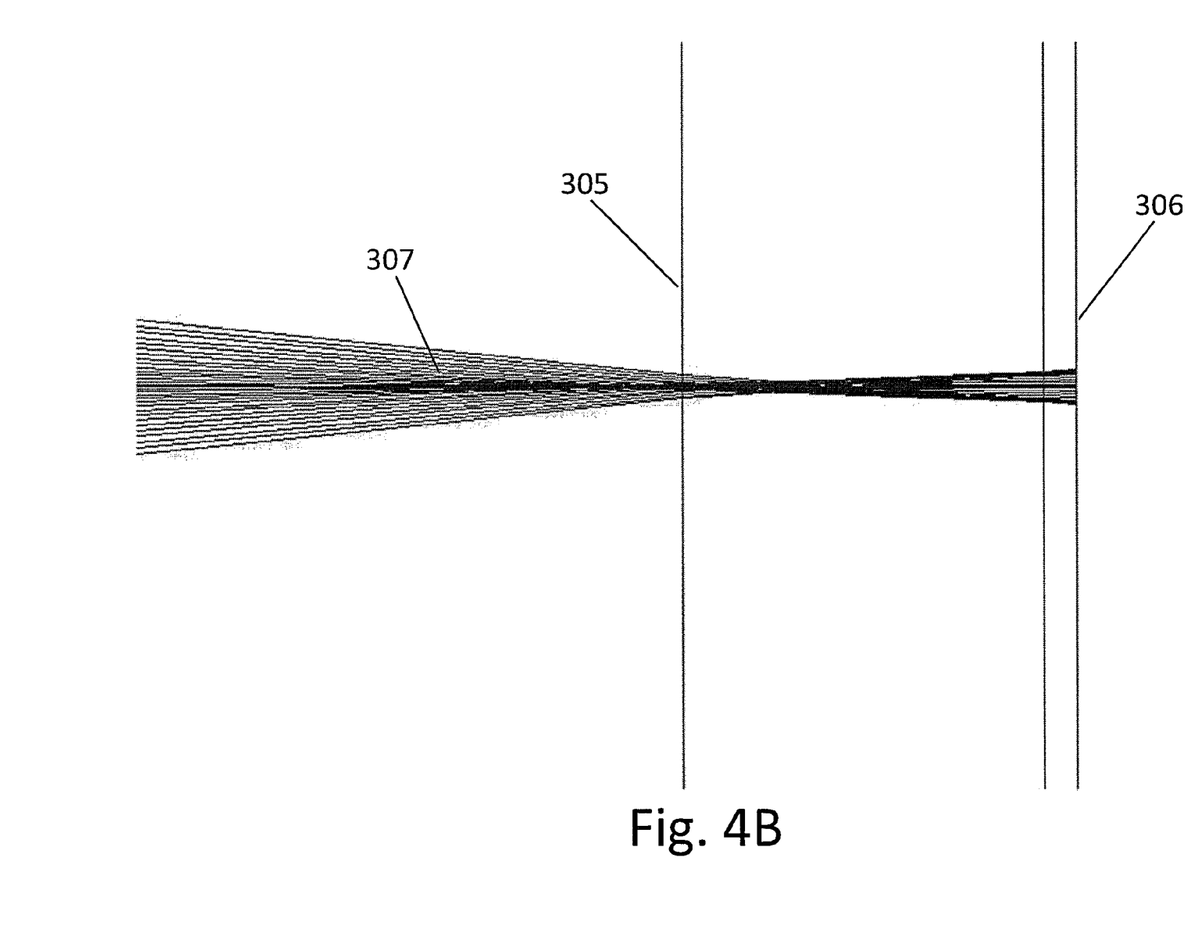

Reference is now made to FIGS. 4A and 4B, which schematically illustrate a focal plane located at the top end of the cover glass and a focal plane located inside the cover glass, respectively, in accordance with embodiments of the present invention. As shown in FIG. 4A, light rays 307 are focused along a distance that begins at a point prior to the top end of cover glass 305, which is the end farthest from imager 306 and extends until the top end of cover glass 305. Light rays 307 are not focused at one single point but instead are focused over a distance. As described above, this is mainly used in order to decrease the dependency of the size of the spot (acquired by imager 306) on the distance between the object and the optical system, e.g., optical system 300.

According to some embodiments, and as shown in FIG. 4B, light rays 307 may be focused along a distance extending within the cover glass 305 instead of at the top end of cover glass 305, which is the end farthest from imager 306 (as shown in FIG. 4A). Once again, this feature is used in order to eliminate the dependency of the size of the spot on the distance of the imaged object from the optical system, e.g. optical system 300. Either of these two different possible locations of the focal plane of an optical system based on EDOF (e.g. optical system 300), may be implemented into in-vivo devices, e.g., capsule endoscopes or traditional endoscopes.

Figure 5:
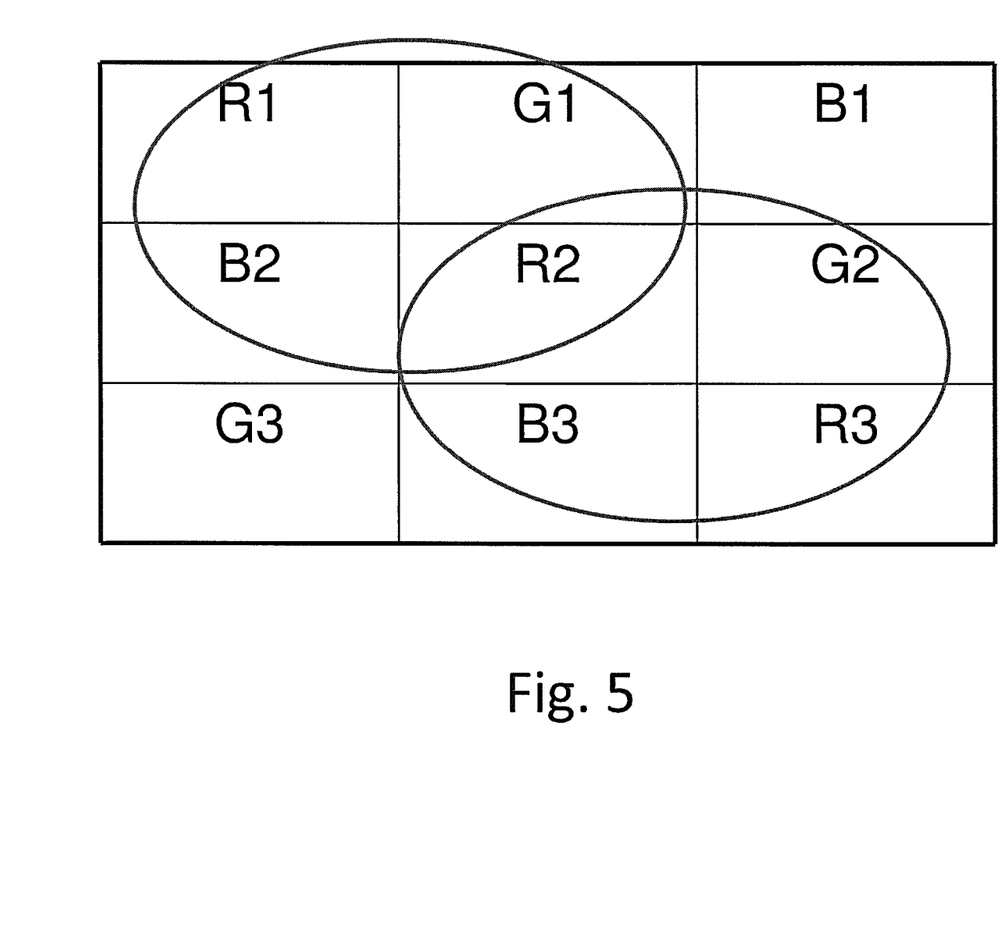
FIG. 5 is a schematic illustration of a filter array, in accordance with embodiments of the present invention.

Reference is now made to FIG. 5, which schematically illustrates a filter array, in accordance with embodiments of the present invention. According to some embodiments, the filter array 303 (of optical system 300) may comprise at least six sub-filters, and in the example shown in FIG. 5, nine sub-filters. The at least six sub-filters may be different from one another, i.e., each of the sub-filters may allow passage of light of a different narrow band wavelength from the rest of the sub-filters.

The sub-filters may be arranged such that any combination of four immediately adjacent sub-filters comprises at least one sub-filter selected from the red spectra, which allows passage of light of the selected red spectrum, at least one sub-filter selected from the green spectra, which allows passage of light of the selected green spectrum, and at least one sub-filter selected from the blue spectra, which allows passage of light of the selected blue spectra. The term "immediately adjacent", specifically regarding four immediately adjacent sub-filters, means that each of the sub-filters directly contacts, at least at one of its corners, every other one of the group of four sub-filters. For example, as shown in FIG. 5, the combination of R1-G2-B2-R2 comprises at least one red sub-filter, at least one green sub-filter, and at least one blue sub-filter. Another combination shown in FIG. 5 is R2-G2-B3-R3, which also comprises at least one red, at least one green, and at least one blue sub-filter.

According to some embodiments, when filter array 303 comprises nine sub-filters, the nine sub-filters may comprise nine different sub-filters, such that each sub-filter is selected from a different wavelength of either the red, green or blue spectra. According to another embodiment, the nine sub-filters may comprise six different sub-filters (selected from either the red, green or blue spectra), while the last three are sub-filters already present among the six different sub-filters. However, the three duplicate sub-filters may comprise at least one sub-filter that corresponds to a wavelength selected from the red spectra, at least one sub-filter that corresponds to a wavelength selected from the green spectra, and at least one sub-filter that corresponds to a wavelength selected from the blue spectra, all of which are already present among the six different sub-filters initially selected.

According to some embodiments, in order to implement optical systems as system 300 in-vivo, the sub-filters of the filter array may be selected from wavelengths that correspond to the absorption spectra of hemoglobin. Absorption spectra of hemoglobin may typically provide information on pathological condition of an in-vivo tissue. In some embodiments, the sub-filters may be selected from the following wavelengths: 420, 470, 510, 540, 560, 570, 600, 620, 630, 660, 800, and 880 nm. In other embodiments, other wavelengths may be selected. In other embodiments, the sub-filters may be selected from wavelengths that correspond to absorption spectra of other in-vivo components, e.g., various biomarkers that may indicate on a biological state of the tissue.

Figure 6A:
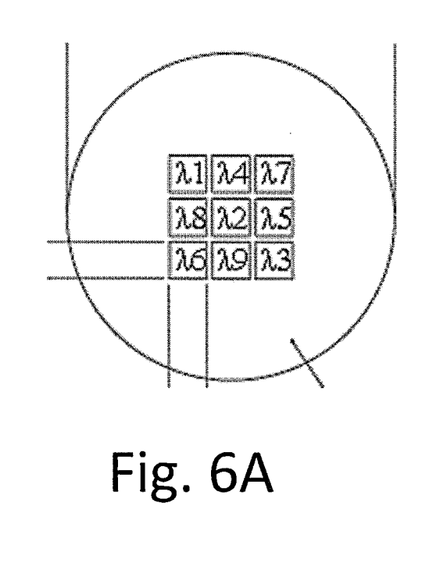
FIGS. 6A-6B are schematic illustrations of two arrangements of sub-filters of the filter array, in accordance with embodiments of the present invention.
Figure 6B:
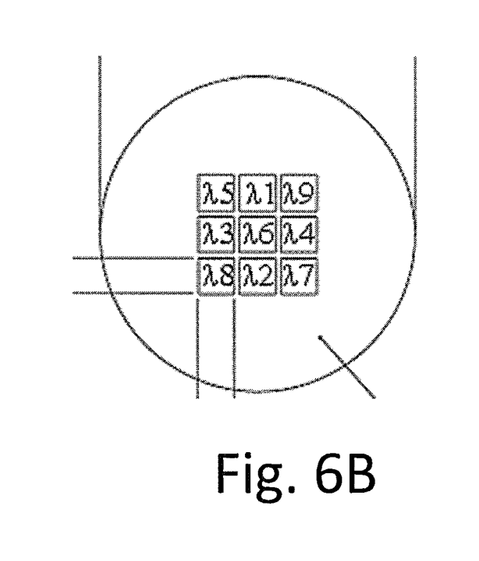

Reference is now made to FIGS. 6A and 6B, which schematically illustrate two possible arrangements of sub-filters of the filter array, in accordance with embodiments of the present invention. FIGS. 6A and 6B both illustrate arrangements of sub-filters such that any four immediately adjacent sub-filters comprise at least one sub-filter selected from the red spectra, at least one sub-filter selected from the green spectra, and at least one sub-filter selected from the blue spectra. According to some embodiments, each of the nine sub-filters is of a different wavelength than the rest of the sub-filters.

The wavelengths of the sub-filters of filter array 303 according to FIG. 6A may be as follows: $\lambda 1=420$ nm, $\lambda 2=470$ nm, $\lambda 3=510$ nm, $\lambda 4=540$ nm, $\lambda 5=560$ nm, $\lambda 6=570$ nm, $\lambda 7=600$ nm, $\lambda 8=620$ nm and $\lambda 9=630$ nm. Other arrangements and other wavelengths may be used. The wavelengths of the sub-filters of filter array 303 according to FIG. 6B may be as follows: $\lambda 1=420$ nm, $\lambda 2=470$ nm, $\lambda 3=540$ nm, $\lambda 4=570$ nm, $\lambda 5=600$ nm, $\lambda 6=620$ nm, $\lambda 7=660$ nm, $\lambda 8=800$ nm and $\lambda 9=880$ nm. Other arrangements and other wavelengths may be used.

Figure 7:
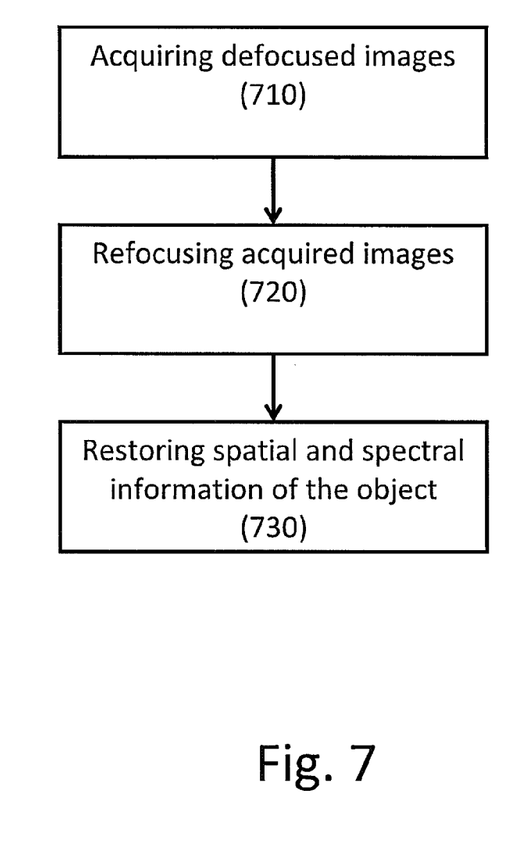
FIG. 7 is a flow chart describing a method for acquiring images containing both spatial and spectral information of an object, in accordance with embodiments of the present invention.

Reference is now made to FIG. 7, which illustrates a flow chart describing a method for acquiring images containing both spatial and spectral information of an object, in accordance with embodiments of the present invention. According to some embodiments, the method may comprise the steps of: acquiring defocused images using an optical system similar to optical system 300 (710), refocusing the acquired images (720), and restoring spatial and spectral information of the imaged object (730), according to the location of the imager's pixel that collected the light, and according to the wavelength of the light collected by the imager, respectively. The sub-filter through which light passes through may determine the wavelengths collected by the pixels of the imager (e.g., imager 306). The location of the pixel along the imager that collected the light may be used to determine the spatial location along the object from which the light was reflected off.

In some embodiments, the step of refocusing the acquired images may be performed by designated software. Refocusing of the acquired images may be done by deconvolution, according to the appropriate point spread function (which translates a point in the plane of the object to a point in the plane of the imager). In some embodiments, the step of restoring spatial and spectral information of the imaged object may be performed by designated software. In some embodiments, the designated software used for restoring spatial and spectral information may be different than the software used to perform refocusing of the images. In other embodiments, the software for restoring spatial and spectral information may be the same software used for refocusing the acquired images.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A system for acquiring images containing spatial and spectral information of an object, the system comprising:
    an extended depth of field optical system;
    a filter array comprising an array of six different sub-filters such that each sub-filter allows the passage of light from a different narrow band of wavelengths of either the red, green or blue spectra, respectively, wherein said six sub-filters are arranged such that any group of four immediately adjacent sub-filters comprises at least one red sub-filter, at least one green sub-filter and at least one blue sub-filter, and wherein said filter array is located at an aperture stop of said optical system;
    a coded mask located at a focal plane of said optical system; and
    an imager located beyond the focal plane such that images acquired by the imager are defocused.

2. The system according to claim 1, wherein said filter array comprises nine different sub-filters.

3. The system according to claim 2, wherein said filter array comprises six different sub-filters, and three different sub-filters that each is a duplicate of one of the six different sub-filters.

4. The system according to claim 1, wherein said sub-filters of said filter array are selected from wavelengths that correspond to absorption spectra of hemoglobin.

5. The system according to claim 4, wherein said sub-filters are selected from the following wavelengths: 420, 470, 510, 540, 560, 570, 600, 620, 630, 660, 800, and 880 nm.

6. The system according to claim 1, wherein said coded mask is a random mask.

7. The system according to claim 6, wherein said coded mask is 40%-60% transmissive and, respectively, 60%-40% closed for passage of light.

8. The system according to claim 6, wherein said coded mask is 50% transmissive for passage of light.

9. The system according to claim 1, wherein said coded mask comprises hyper-pixels arranged at groups of three over three hyper-pixels.

10. The system according to claim 9, wherein said coded mask is arranged such for any three over three hyper-pixels at least one hyper-pixel is open and at least one hyper-pixel is closed.

11. The system according to claim 1, wherein said focal plane is located at a top end of a cover glass of the imager.

12. The system according to claim 1, wherein said imager is a black and white imager.

13. A capsule endoscope comprising the system according to claim 1, wherein the location of said focal plane is at a top end of a cover glass of the imager or inside the cover glass of the imager, and wherein said coded mask is located at the top end of the cover glass of the imager.

14. A method for acquiring images containing spatial and spectral information of an object, the method comprising:
    acquiring defocused images using the system according to claim 1;
    refocusing said acquired defocused images; and
    restoring spatial and spectral information of the object according to the location of the imager's pixel that collected the light, and according to the wavelength of the light collected by the imager, respectively.

15. The method according to claim 14, wherein refocusing of the defocused images is performed by designated software.

16. The method according to claim 14, wherein restoring spatial and spectral information of the object is performed by designated software.

\* \* \* \* \*